US008795300B2

(12) United States Patent
Bilotti et al.

(10) Patent No.: US 8,795,300 B2
(45) Date of Patent: Aug. 5, 2014

(54) ANASTOMOTIC DEVICE

(75) Inventors: Federico Bilotti, Aprillia (IT);
Alessandro Pastorelli, Rome (IT);
Michele D'Arcangelo, Rome (IT);
Brian James Thompson, Cincinnati,
OH (US); Roberto Tacchino, Rome (IT)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1169 days.

(21) Appl. No.: 12/279,549

(22) PCT Filed: Feb. 14, 2007

(86) PCT No.: PCT/EP2007/001272
§ 371 (c)(1),
(2), (4) Date: Oct. 16, 2008

(87) PCT Pub. No.: WO2007/101526
PCT Pub. Date: Sep. 13, 2007

(65) Prior Publication Data
US 2010/0063520 A1      Mar. 11, 2010

(30) Foreign Application Priority Data

Mar. 7, 2006   (IT) .............................. MI2006A0410

(51) Int. Cl.
*A61B 17/08*       (2006.01)
(52) U.S. Cl.
USPC ........................................................ 606/153
(58) Field of Classification Search
USPC ................. 606/151, 153–156, 215, 216, 217;
3/151, 153–156
See application file for complete search history.

(56) References Cited

U.S. PATENT DOCUMENTS

| | | | | |
|---|---|---|---|---|
| 2,428,918 A | * | 10/1947 | Miller | 606/154 |
| 3,155,095 A | * | 11/1964 | Brown | 606/154 |
| 3,254,650 A | * | 6/1966 | Collito | 606/153 |
| 3,254,651 A | * | 6/1966 | Collito | 606/153 |
| 3,316,914 A | * | 5/1967 | Collito | 606/150 |
| 3,771,526 A | | 11/1973 | Rudie | |
| 4,214,586 A | * | 7/1980 | Mericle | 606/154 |

(Continued)

FOREIGN PATENT DOCUMENTS

WO    WO 01/54594 A    8/2001
WO    WO 02/13699 A    2/2002

OTHER PUBLICATIONS

International Search Report dated Apr. 13, 2007, International Application No. PCT/EP2007/001272.

(Continued)

*Primary Examiner* — Julian W Woo

(57) ABSTRACT

The present invention relates to an anastomotic device (10) comprising a first ring (20) having a first contact surface (21) and a second ring (30) having a second contact surface (31). The rings (20, 30) are suitable to be approached in the axial direction (X) such as to move said contact surfaces (21; 31) towards each other. The anastomotic device is characterized in that the contact surfaces (21, 31) have an undulated shape relative to a plane (π) perpendicular to the axis (X) of the rings (20, 30). According to another aspect thereof, the invention also relates to an apparatus (60) for the implantation of the anastomotic device (10). According to a further aspect thereof, the invention relates to a kit comprising an anastomotic device (10) and an apparatus (60) for the implantation of the same.

23 Claims, 8 Drawing Sheets

(56) References Cited

U.S. PATENT DOCUMENTS

| | | | | |
|---|---|---|---|---|
| 4,233,981 A | * | 11/1980 | Schomacher | 606/153 |
| 4,294,255 A | * | 10/1981 | Geroc | 606/153 |
| 4,366,819 A | * | 1/1983 | Kaster | 606/153 |
| 4,523,592 A | * | 6/1985 | Daniel | 606/153 |
| 4,917,091 A | * | 4/1990 | Berggren et al. | 606/153 |
| 4,930,502 A | * | 6/1990 | Chen | 606/150 |
| 5,250,058 A | * | 10/1993 | Miller et al. | 606/154 |
| 5,336,233 A | * | 8/1994 | Chen | 606/153 |
| 5,456,714 A | * | 10/1995 | Owen | 623/1.31 |
| 5,690,656 A | * | 11/1997 | Cope et al. | 606/153 |
| 6,235,058 B1 | * | 5/2001 | Huene | 623/13.14 |
| 6,254,618 B1 | | 7/2001 | Dakov | |
| 6,503,258 B1 | * | 1/2003 | Filho | 606/153 |
| 6,736,825 B2 | * | 5/2004 | Blatter et al. | 606/153 |
| 6,749,622 B2 | * | 6/2004 | McGuckin et al. | 606/213 |
| 6,805,708 B1 | * | 10/2004 | Yencho et al. | 623/1.3 |
| 6,811,555 B1 | * | 11/2004 | Willis et al. | 606/153 |
| 7,160,311 B2 | * | 1/2007 | Blatter et al. | 606/153 |
| 7,615,064 B2 | * | 11/2009 | Bjerken | 606/153 |
| 7,901,417 B2 | * | 3/2011 | Blatter et al. | 606/153 |
| 2001/0023354 A1 | * | 9/2001 | Blatter et al. | 606/153 |
| 2002/0082625 A1 | | 6/2002 | Huxel et al. | |
| 2003/0153932 A1 | | 8/2003 | Spence et al. | |
| 2004/0004105 A1 | | 1/2004 | Jankowski | |

OTHER PUBLICATIONS

European Search Report dated May 12, 2011, EP Application No. EP 11 16 1084.

\* cited by examiner

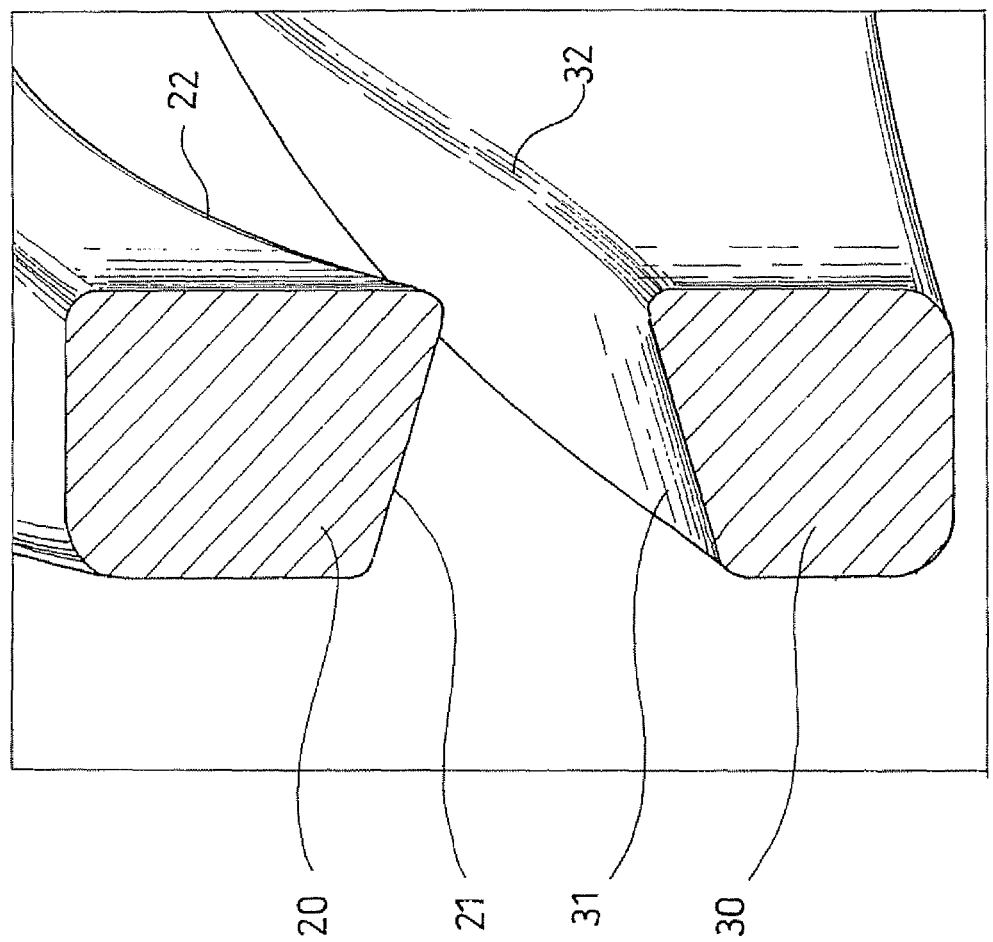

ANASTOMOTIC DEVICE

The object of the present invention is an anastomotic device to carry out anastomoses, particularly to carry out anastomoses of the digestive tube or blood vessels.

According to further aspects, an implant apparatus suitable to implant the anastomotic device and an operation kit comprising the anastomotic device and the implant apparatus are also objects of this invention.

BACKGROUND OF THE INVENTION

A known example of an anastomotic device comprising two metallic rings suitable to be approached to each other in the axial direction is disclosed in U.S. Pat. No. 4,233,981. The two rings comprise tips suitable to hold in the desired position the pieces of the conduit walls on which the anastomosis is carried out. The two rings further comprise a screw-nutscrew coupling suitable to fasten both rings to each other, such that the pieces of the conduit walls are clamped therebetween.

The known devices, such as that described above, are not without drawbacks.

In fact, they allow obtaining a lumen having a relatively small size as compared with the overall size of the device. Particularly, the operating diameter of the lumen that can be obtained with these known devices has the inner diameter of the rings forming the device as its highest limit.

This entails the disadvantage of having to operate with relatively large-sized devices in order to carry out the anastomosis operation in a successful manner. The use of small-sized devices would in fact allow creating a potentially insufficient lumen with a consequent risk of stenosis which would make the whole anastomosis operation useless.

A lumen with an operating inner diameter being limited by the inner diameter of the rings is particularly uncomfortable when the type of operation employed requires the equipment to be withdrawn through the lumen. In this case, in fact, the edge of the lumen just created may be subjected to stress in order to release the equipment. This stress may be traumatic and generate stenosis or other complications during the operation.

Even if the type of operation does not require any equipment to pass through the lumen, the restraint imposed to the lumen size sensibly affects the effectiveness of the operation, mainly when stenosis or other complications occur.

Accordingly, the need is felt to have an anastomotic device allowing to overcome, at least partially, said the described drawbacks.

The problem at the heart of the present invention is thus to provide an anastomotic device which has such structural and functional characteristics as to meet said requirement.

BRIEF DESCRIPTION OF THE DRAWINGS

Further characteristics and advantages of the anastomotic device, implant apparatus and kit according to the invention will become apparent from the following description of preferred exemplary embodiments thereof, which are merely illustrative and non-limiting, with reference to the annexed figures, in which:

FIG. 6.a illustrates an enlarged view of the detail indicated with VI.A in FIG. 6;

DETAILED DESCRIPTION OF THE INVENTION

Figure 1:
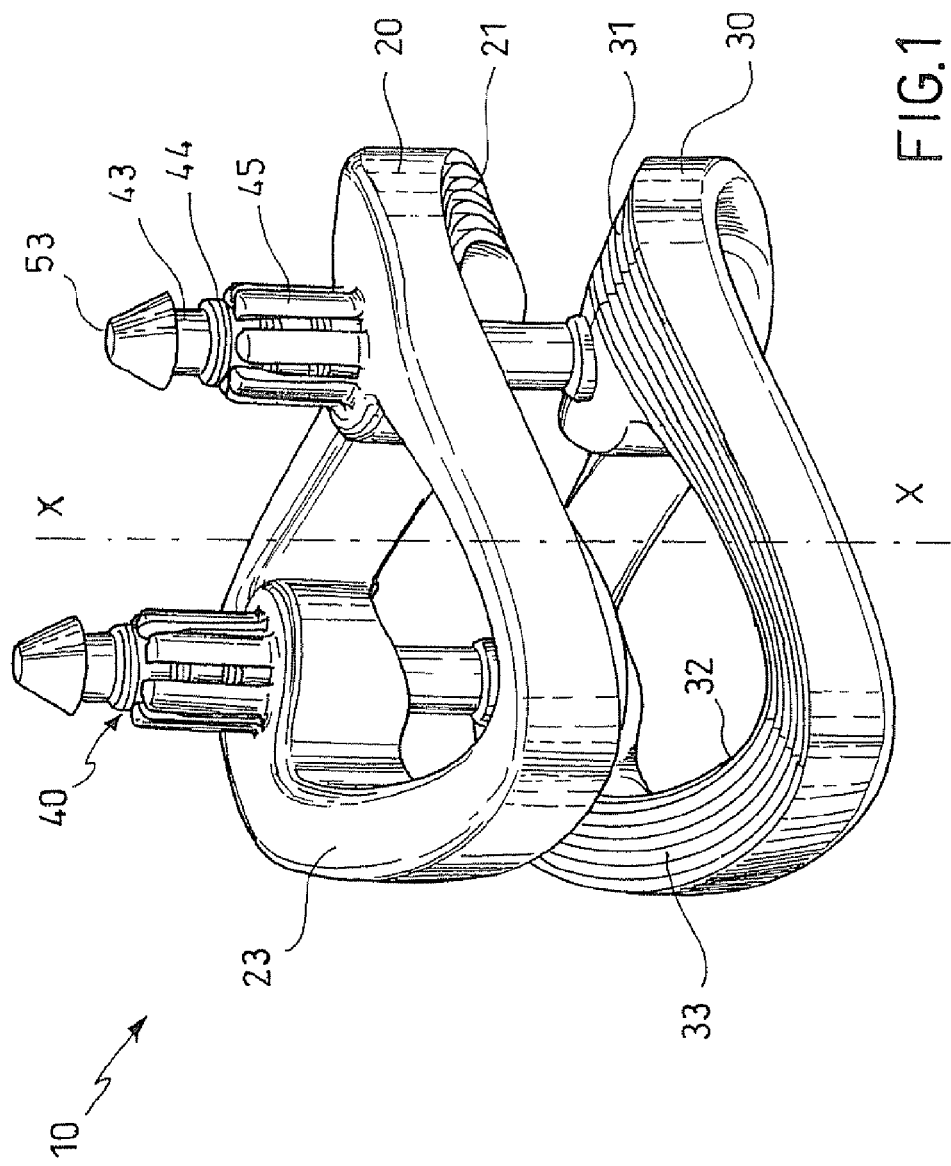
FIG. 1 illustrates a perspective view of an embodiment of an anastomotic device in accordance with the present invention.

With reference to said figures, with 10 has been generally designated an anastomotic device in accordance with the present invention. The device 10 comprises a first ring 20 having a first contact surface 21 and a second ring 30 having a second contact surface 31.

Each of the rings 20 and 30 univocally defines an axis X. The direction of a straight line parallel to the axis X is called the "axial" direction. The direction of a half-line perpendicular to the axis X and originating therefrom is called the "radial" direction. Finally, a circumference centred on the axis X and arranged on plane perpendicular thereto defines the "circumferential" direction.

In FIG. 1, the rings 20 and 30 are arranged in the configuration of use, such that the respective axes X coincide. The ring 20 and 30 are suitable to be mutually approached to each other in the axial direction, such that the contact surfaces 21 and 31 are approached to each other.

Figure 5:
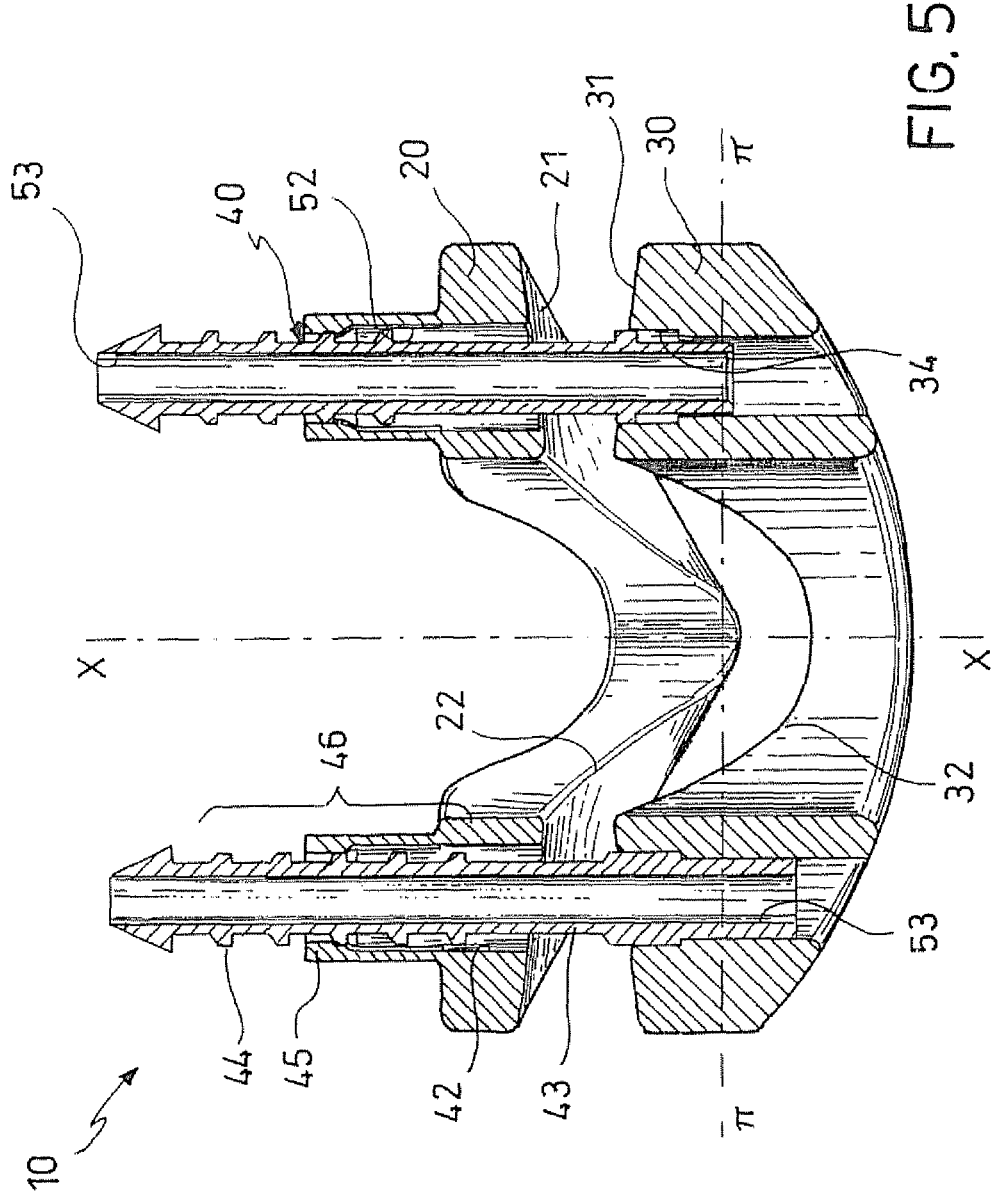
FIG. 5 illustrates a view of an anastomotic device in accordance with the present invention being sectioned along a trace similar to that indicated with V-V in FIG. 4.
Figure 6:
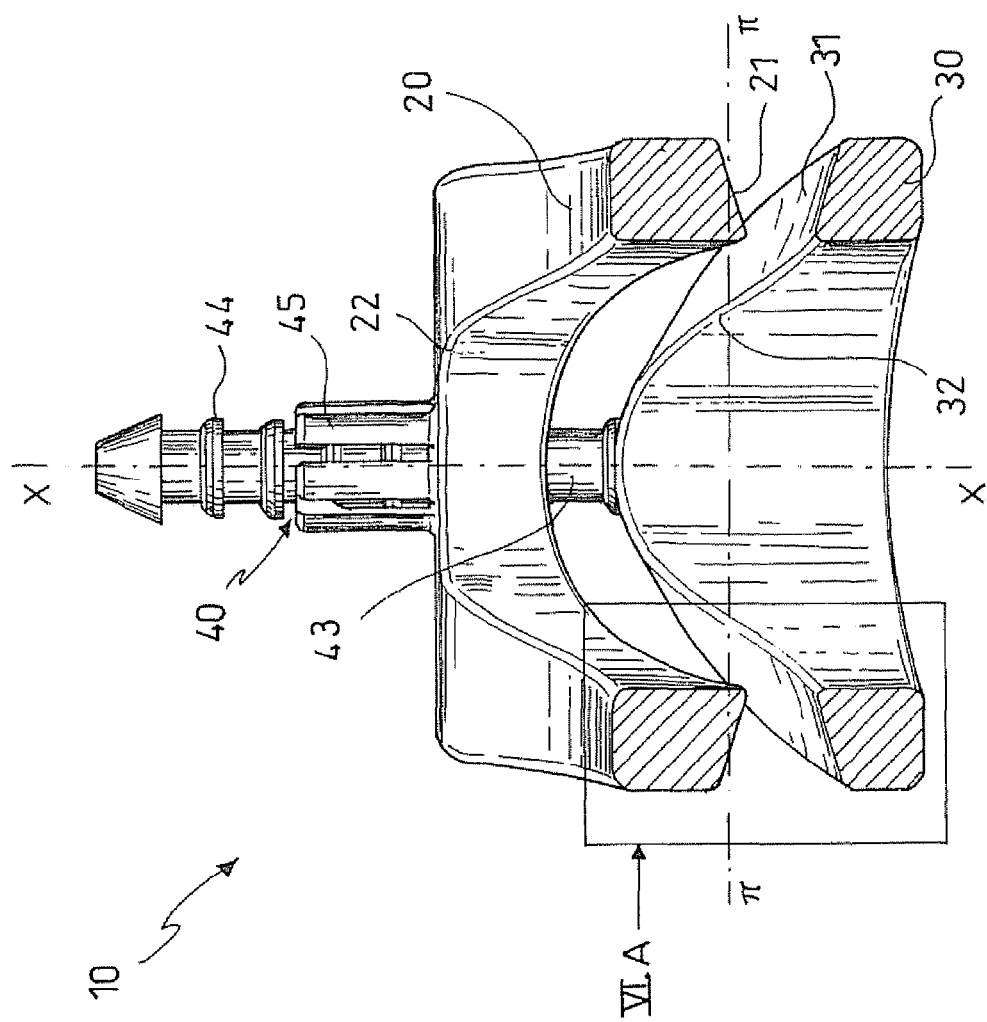
FIG. 6 illustrates a view of an anastomotic device in accordance with the present invention being sectioned along a trace similar to that indicated with VI-VI in FIG. 4.

The contact surfaces 21 and 31 have an undulated shape relative to a plane $\pi$ perpendicular to the axes X of the rings 20 and 30 (see for example FIGS. 5 and 6).

Figure 3:
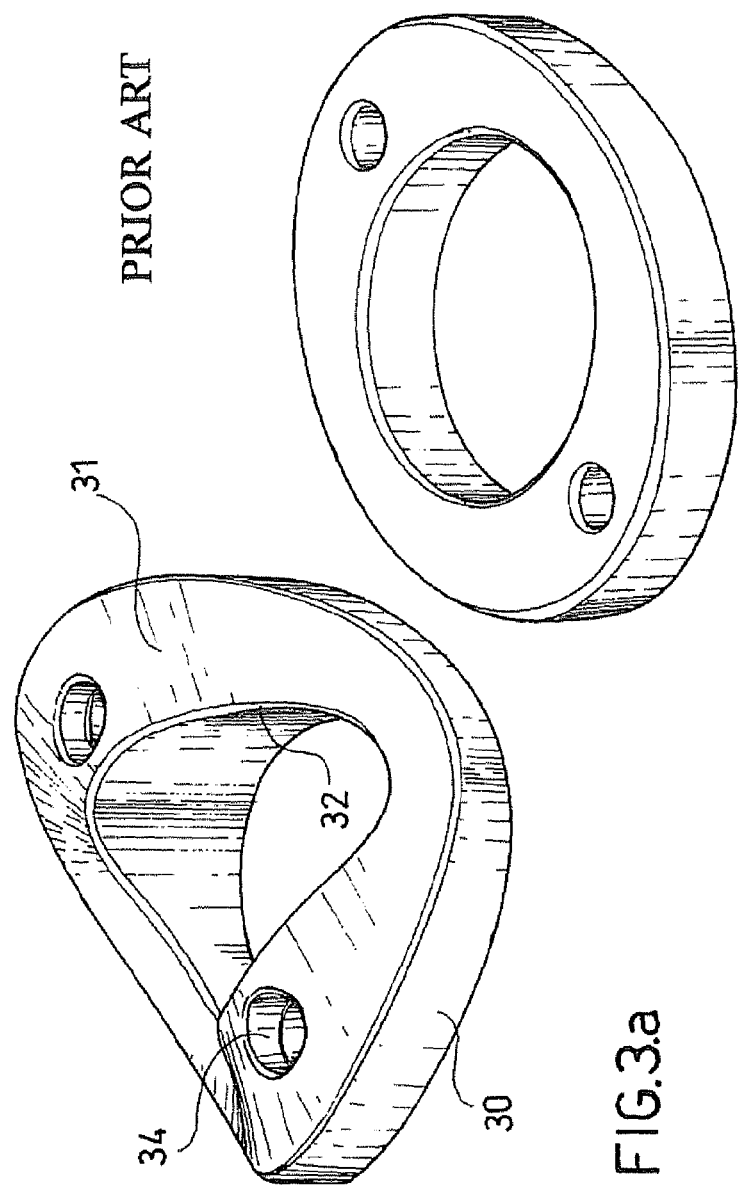
FIGS. 3.a and 3.b illustrate a ring of an anastomotic device in accordance with the present invention in comparison with a ring of an anastomotic device of a known type.

In other words, while the contact surfaces of the known rings (see for example FIG. 3.b) lay on plane $\pi$, the contact surfaces 21 and 31 of the rings 20 and 30 according to the invention deviate from the plane $\pi$ to lay on a curved surface (see for example FIG. 3.a).

This characteristic implies a large number of advantages for an anastomotic device 10 according to the invention as compared with an anastomotic device of a known type having the same size.

Figure 4:
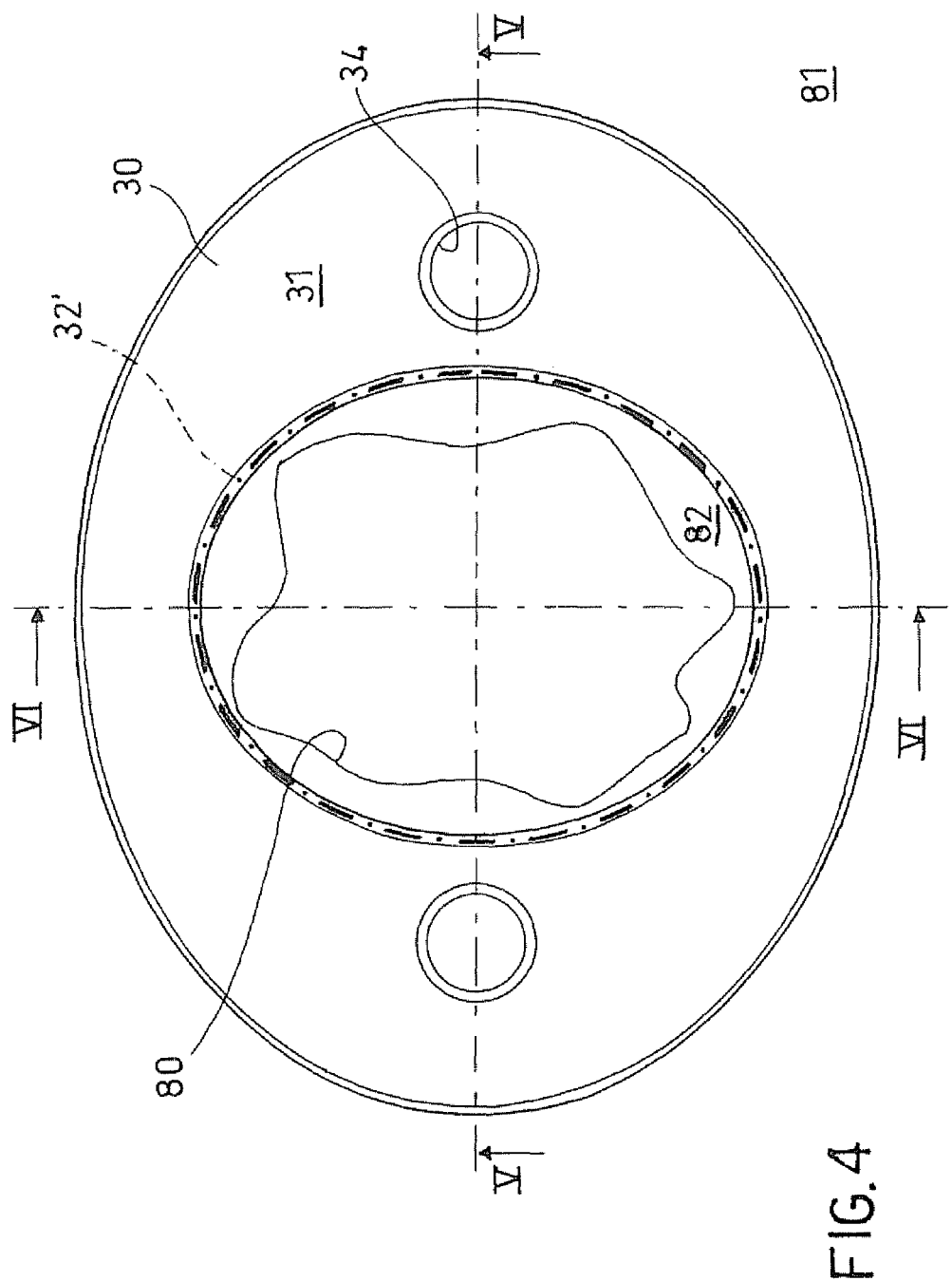
FIG. 4 illustrates a ring of an anastomotic device in accordance with the present invention during an implant step.

By "same size" is meant herein and below that the rings involved in the comparison (such as those in FIGS. 3.a and 3.b) have the same projection in the axial direction (for example, that in FIG. 4).

As the contact surfaces 21 and 31 diverge from the plane development of the known surfaces, their respective inner edges 22 and 32 are defined by three-dimensional loops which have a greater length (or development) than the plane curve 32' (see FIG. 4) which represents the projection thereof in the axial direction.

On the other hand, as the known contact surfaces have a plane development, their respective inner edges are defined by bidimensional loops which have a length (or a development) exactly equal to the plane curve which represents the projection thereof in the axial direction.

The end size of the lumen 80 obtained in the anastomosis directly derive from the length of the inner edges of the contact surfaces. Carrying out the discussion with an effective simplification, the final anastomosis lumen 80 can be considered as having a round shape. The circumference of this round-shaped artificial lumen would have a length equal to the inner edges of the contact surfaces of plane anastomotic rings having a greater size.

In view of the above, it appears that the anastomotic device 10 according to the invention allows obtaining final lumens having a greater size than those obtained with a known device having the same size.

Furthermore, the anastomotic device 10 according to the invention allows obtaining final lumens having a greater elasticity than those obtained with a known device.

With reference to FIG. 3, and with the other conditions being equal, the three-dimensional loop defining the inner edge 32 of the undulated contact surface 31 has a greater length than the length of the plane curve (ellipse) defining the inner edge of the known contact surface.

The anastomotic device 10 according to the invention, when properly implanted, is capable of holding the rings 20 and 30 close to each other, and thus holding the pieces of the walls 81 of the conduits involved in the anastomosis operation close to each other. The device 10 holds the rings 20 and 30 and the pieces of the walls 81 close to each other due to the clamping force it can ensure.

Furthermore, the anastomotic device 10 holds the pieces of the walls 81 in the proper mutual position substantially due to the frictional force generated between the contact surfaces 21 and 31 and the walls 81 of the conduits.

The fact that the contact surfaces 21 and 31 are not plane determines an increase in their contact area with the conduit walls 81. Accordingly, the total force holding the pieces of the conduit walls 81 in position, and which thus ensures the proper course of the anastomosis operation, is considerably increased.

With reference to FIG. 3, the undulated contact surface 31 determines a contact area with the conduit walls that is greater than the contact area determined by the known plane contact surface.

In accordance with an embodiment of the invention, the effect of the frictional force is further facilitated by the provision of knurlings 33 (see for example FIG. 1), pyramidal or conical relieves, or other surface finishing suitable to increase the sliding friction.

In accordance with an embodiment of the invention, the anastomotic device 10 comprises coupling means 40 that are suitable to generate and maintain a clamping force in the axial direction between the first ring 20 and the second ring 30 when they have been implanted.

The coupling means 40 are preferably of a snap-type such as illustrated in the annexed figures. The snap coupling means are simply actuated by approaching the rings 20 and 30 to each other and pressing them against each other in the axial direction with the force required to overcome the elastic resistance of the snaps and press the tissues comprised between the rings 20 and 30.

This characteristic of the snap coupling means is particularly convenient, since it allows for easy operation also when one of the two rings (typically the one being in the distal position) cannot be directly accessed by the operator.

Due to this advantage, the anastomotic device 10 according to the invention, provided with snap coupling means, is particularly suitable when the anastomosis operation is carried out following the endoluminal or laparoscopic route, instead of traditional open surgery.

With reference to the annexed figures, the coupling means 40 comprise two pins 43 projecting from the second ring 30 in the axial direction towards the contact surface 31 facing direction.

The pins 43 can be made as one piece with the ring 30 or, preferably, they can be assembled thereto. For example, the pins 43 can be threaded within suitable seats 34 that are formed on the ring 30.

The pins are provided with teeth 44, which are distributed along an operating coupling tract 46 (see FIG. 5).

Again, the coupling means 40 comprise two seats that are formed on the first ring 20 with axial development. The seats 42 are suitable to house the pins 43 and are provided with elastic tabs 45. The elastic tabs 45 are, in turn, suitable to sequentially engage the teeth 44 and thus run in one way only along the operating coupling tracts 46.

In view of the description, it will be apparent to those skilled in the art that, after the two rings 20 and 30 have been approached to each other, the pins 43 have been fitted within the seats 42 and the desired clamping force has been applied in the axial direction, the elastic tabs 45 slide along the operating coupling tracts 46 and engage the teeth 44. As the elastic tabs 45 cannot slide in the opposite direction, they prevent the rings from moving away again in the axial direction.

The embodiment illustrated in the annexed figures comprise two pins 43 and two respective seats 42. Similarly, a different number of pins and seats can be arranged in order to meet particular requirements.

In the embodiments represented in the annexed figures, the provision of two pins 43, which are stably housed in the seats 42, prevents any possible relative movement between the two rings 20 and 30 in the circumferential direction.

In other possible embodiments, in which only one pin 43 is provided, the relative movement between the two rings 20 and 30 in the circumferential direction must be otherwise prevented, such as by means of a pin section other than round.

With particular reference to those embodiments that are intended for endoluminal or laparoscopic use, the anastomotic device 10 comprises holes 52 and 53 suitable for the guide wires to pass therethrough, which are required to carry out the operation. The holes 52 and 53 are formed on both rings 20 and 30, such as to allow the same to be properly approached to each other simply by sliding along the guide wires.

In the example of the annexed figures, as regards the first ring 20, the seats 42 act as the holes 52 for the guide wires to pass therethrough.

As regards the second ring 30, the seats 34 of the pins 43 act as the holes 53 for the guide wires to pass therethrough. The holes 53 are then continued within the pins 43.

The endoluminal or laparoscopic operation method provides, in a manner known per se, that the guide wires allow the two rings 20 and 30 to be properly positioned relative to each other. At the same time, by pulling the guide wires, when desired, a clamping force is provided which acts on the distal ring in the direction of the proximal ring.

In order to make the clamping effective, an equal and opposite force must be obviously provided, which acts on the proximal ring in the direction of the distal ring. This equal and opposite force is obtained by pushing the proximal ring by means of an implant apparatus 60 according to the invention, which will be described below.

In accordance with several possible embodiments of the device 10, such as that represented in FIG. 1, the coupling means 40 are formed within the curves defining the inner edges 22 and 32 of the contact surfaces 21 and 31.

In accordance with several possible embodiments of the anastomotic device 10, such as that in FIGS. 6 and 6.a, the surfaces 21 and 31 are mutually inclined. As may be clearly seen particularly in FIG. 6.a, the mutual inclination of the surfaces is such that a spacing is generated between the contact surfaces 21 and 31 that is variable in the radial direction.

This development of the contact surfaces 21 and 31 defines a variable development also in the pressure values of the tissues 82 that are comprised between the rings 20 and 30.

Specifically, the radially innermost region of the surfaces 21 and 31, i.e. the one proximate to the inner edges 22 and 32, gives the highest pressure. In accordance with the device 10 in FIG. 6.*a*, the pressure decreases in the radial direction towards the outside and reaches a minimum at the outer edges of the surfaces 21 and 31.

The success or failure of the anastomosis may be determined by the fact of being able to obtain the proper pressure value to be applied by the anastomotic device 10 to the tissues 82.

In fact, an excessive pressure on the tissues 82 determines a decrease in the blood flow, which leads to the necrosis of these tissues. This event often implies undesired side effects, and consequently, it is preferably avoided. At the same time, an insufficient pressure on the tissues 82 does not allow holding the tissue pieces in an effective manner, and may cause the same to move away from each other. When the tissues move away from each other, the anastomosis experiences the so-called leak effect.

Setting the proper pressure value upon implantation is made even harder since, practically, the operator imposes a distance between the rings 20 and 30 from which the pressure of the tissues 82 is derived. The pressure value thus depends on the difference between the thickness of the undisturbed tissues 82 and the distance imposed between the rings 20 and 30.

Due to the possibility of obtaining, in the circumferential direction, a range of pressure values distributed in the radial direction, the user can more easily obtain the proper value.

Similarly, in order to meet other specific requirements, other profiles can be studied for the radial section of the contact surfaces 21 and 31, such that other developments are obtained for pressure force variation.

Moreover, the fact that the surfaces 21 and 31 are mutually inclined determines a further increase in the contact region with the conduit walls as compared with the contact region being determined by the plane contact surfaces.

Figure 2:
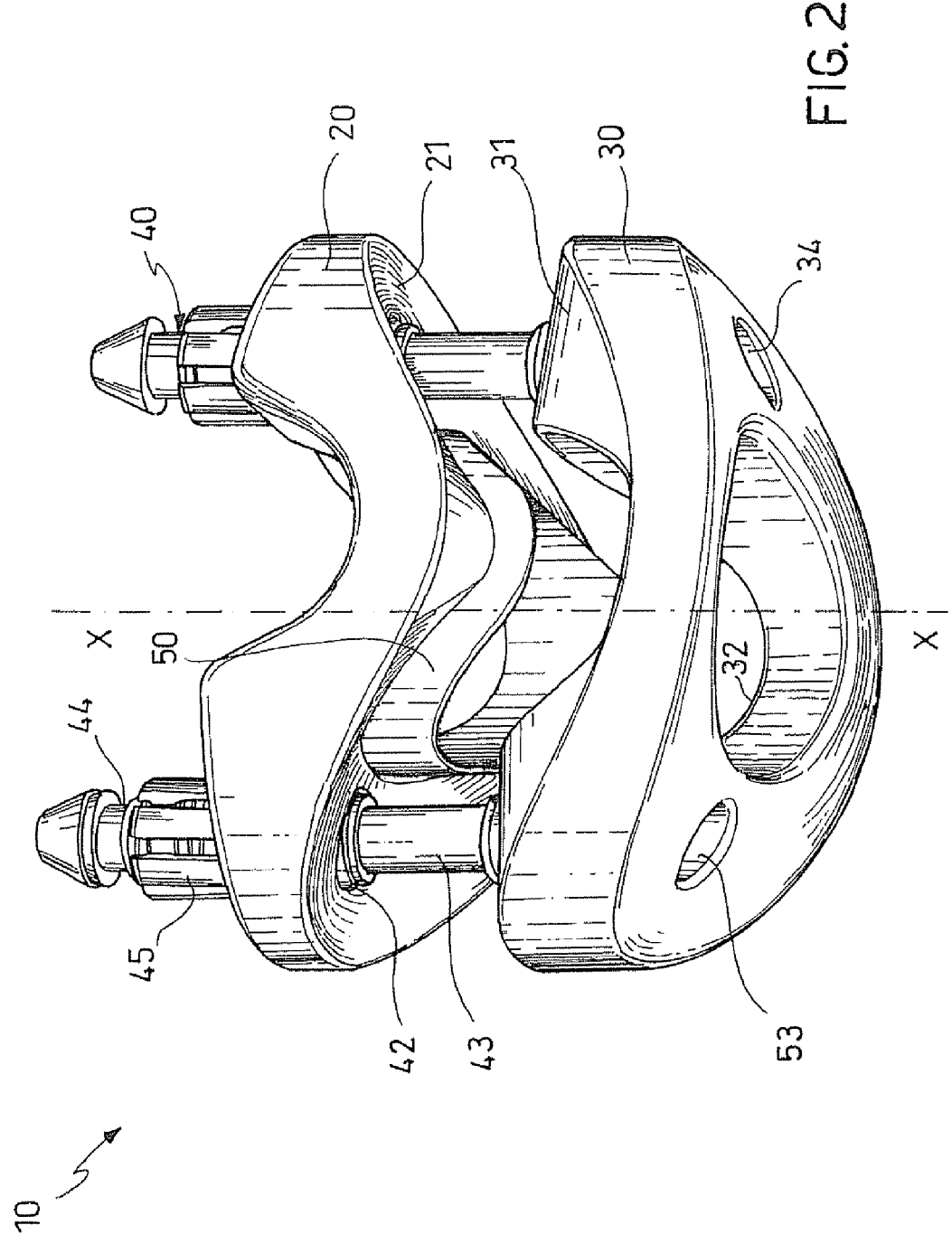
FIG. 2 illustrates a perspective view of another embodiment of an anastomotic device in accordance with the present invention.

In accordance with other possible embodiments of the anastomotic device 10, for example that in FIG. 2, a knife 50 is arranged on one of the rings. Advantageously, the knife 50 is arranged at the inner edge of the contact surface.

In the example from FIG. 2, the knife 50 is arranged on the first ring 20, but nothing prevents it from being arranged on the second ring 30. The knife 50 has such an extension in the axial direction that it can cooperate, when the rings are being approached to each other, with the inner edge 32 of the surface 31. When the two rings 20 and 30 are moved proximate to each other, such as when the device 10 is being implanted, the knife 50 and edge 32 act like an annular shear.

When the required clamping force is applied, the knife 50 and edge 32 automatically open the desired lumen 80 in the walls 81 of the conduits involved in the anastomosis. Thereby, further surgery is no longer required in order to remove the portion of inner tissue 82 of the desired lumen 80.

The anastomotic device 10 can be made of any type of material suitable for surgical applications.

Particularly, both the first ring 20 and the second ring 30 can be made of a non bio-absorbable material, such as a plastic or metallic material. In this case, the anastomotic device 10 is definitively fixed in position in the site where it has been fitted. In this case, the anastomotic device 10 spontaneously detaches and moves away only when it necrotizes the tissue to which it is attached.

Alternatively, the selection of the material for the whole anastomotic device 10 can be addressed to a bio-absorbable or biofragmentable material, thus providing that the anastomotic device 10 is completely absorbed after a determined period of time.

Finally, the anastomotic device 10 can be partially made of bio-absorbable or biofragmentable material. Particularly, it is advantageous to provide manufacturing the coupling means 40 of bio-absorbable or biofragmentable material, such that the anastomotic device 10 is allowed to detach from the site in which it has been applied after a determined period of time and move away in a spontaneous manner.

In the case illustrated in the annexed drawings, the pins 43 and/or the seats 42 and/or the elastic tabs 45 and/or the teeth 44 may be advantageously provided to be made of bio-absorbable or biofragmentable material.

Due to this characteristic, an anastomosis can be obtained, after the required post-surgery course has elapsed, which is free from any implant of foreign material to the tissues 82 in the vicinity of lumen 80.

Again, the constriction formed by the rings 20 and 30 about the lumen 80 being eliminated, the latter can freely adopt its final definitive size, in view of what has been discussed above. Due to this final size the anastomosis is definitively provided with all the effectiveness desired during the operation planning step.

As those skilled in the art will appreciate from the above description, the anastomotic device 10 according to the invention can be used in endoluminal operations, laparoscopy operations or operations carried out by means of open surgery techniques.

Figure 7:
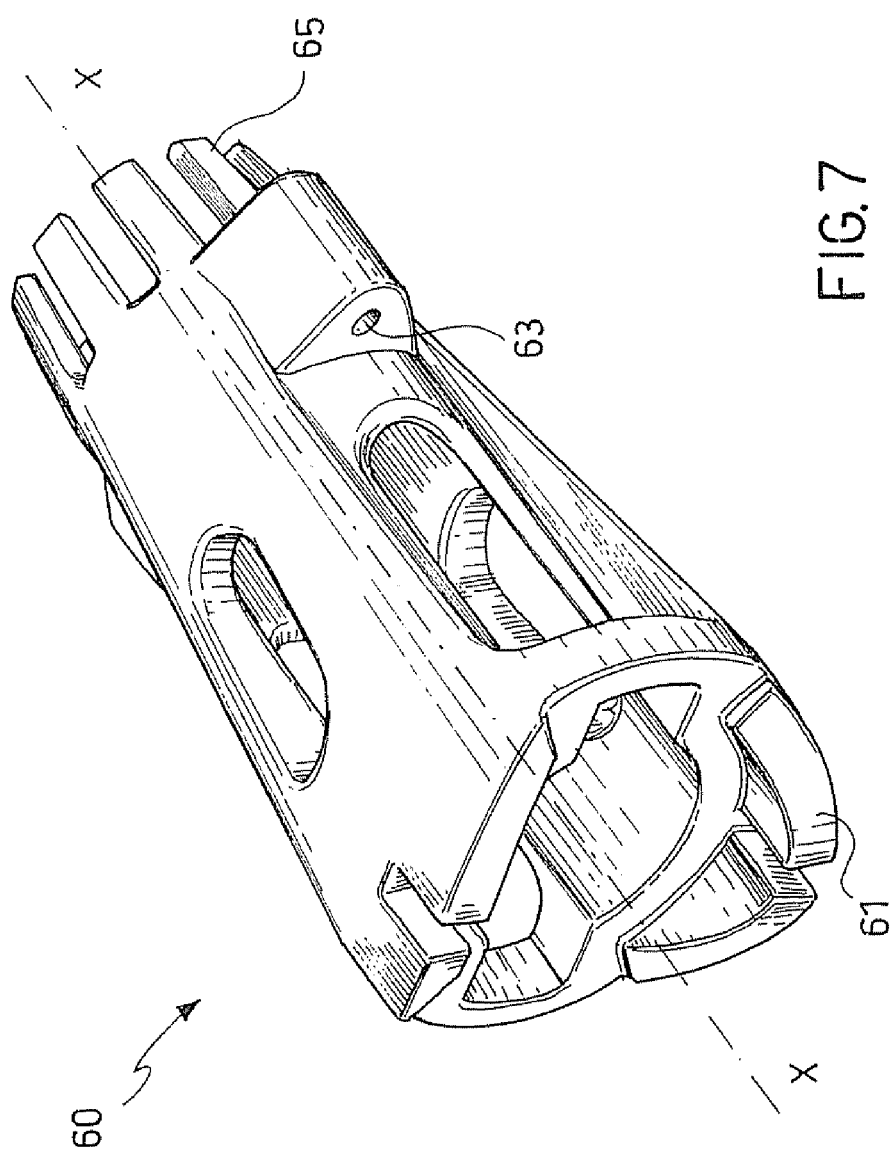
FIG. 7 illustrates a perspective view of an apparatus for the implantation of an anastomotic device in accordance with the present invention.

Another aspect of the present invention relates to the apparatus 60 for implanting the anastomotic device 10 as described above. As can be clearly seen in FIG. 7, the implant apparatus 60 has a development that is mainly oriented along an axis. This axis is called herein the axis "X", because upon use it coincides with the axes of the rings 20 and 30 of the device 10.

The implantation device 60 is suitable to provide the ring of the device 10 that is placed in a proximal position, i.e. the first ring 20, with an even thrust.

Particularly, the apparatus 60 comprises a thrust surface 61 that is suitable to rest, in the axial direction, on the service surface 23 opposite the support surface 21 of the ring 20. The thrust surface 61 is totally complementary to the service surface 23, such as to be able to adhere to a wide percentage of the same.

It is also important that the contact points and/or regions of the thrust surface 61 with the service surface 23 are distributed in a balanced manner, both in the circumferential direction and in the radial direction. This allows maintaining the thrust by the implant apparatus 60 on the ring 20 balanced and preventing the generation of moments and/or forces other than the desired axial force.

In accordance with an embodiment thereof, the apparatus 60 comprises holes 63 for the guide wires that are used for the operation of endoluminal or laparoscopic implantation of the device 100 to be passed therethrough. The holes 63 allow a proper placement of the ring 20 relative to the implant apparatus 60 simply by means of sliding along the guide wires. In this embodiment, the implant apparatus 60 advantageously comprises means 65 for attachment to a laparoscope or endoscope.

A further aspect of the present invention relates to a kit 70 comprising an anastomotic device 10 and an apparatus 60 for the implantation of the same.

To the embodiments of the anastomotic device 10 and the apparatus 60 for the implantation of the same as described above, those skilled in the art, aiming at satisfying contingent and specific needs, may carry out number of modifications, adaptations and replacements of elements with others functionally equivalent, without however departing from the scope of the claims below.

The invention claimed is:

1. An anastomotic device (10) comprising:
a first ring (20) having a first contact surface (21); and
a second ring (30) having a second contact surface (31);
said first and second rings (20, 30) being suitable to be approached to each other in an axial direction of an axis (X) such as to move said contact surfaces (21, 31) towards each other;
coupling means adapted to couple the first and second rings (20, 30) to each other for said first and second contact surfaces (21, 31) to clamp tissue walls intended to be anastomosed,
wherein said contact surfaces (21, 31) extend radially to said axis (X) from inner edges (22, 32) to outer edges (21, 31), said outer edges (21, 31) forming radially outer free edges of said first and second rings (20, 30),
wherein said contact surfaces (21, 31) have a circumferentially undulated shape relative to a plane (π) perpendicular to the axis (X) of said first and second rings (20, 30), said circumferentially undulated shape extending throughout the entirety of said contact surfaces (21, 31) including said inner edges (22, 32) and outer edges (21, 31), and said coupling means being arranged radially inside the outer edges (21, 31), in which, when the first and second rings (20, 30) are coupled to each other, the first and second contact surfaces (21, 31) define a spacing therebetween which increases radially from a minimum axial spacing between inner edges (22, 32) to a maximum axial spacing between outer edges of said contact surfaces (21, 31) in a radial cross-section with respect to the axis (X).

2. The anastomotic device (10) according to the preceding claim, wherein the contact surfaces (21, 31) of the rings (20, 30) are curved surfaces.

3. The anastomotic device (10) according to claim 2, wherein said inner edges (22, 32) are defined by three-dimensional loops having a greater length than the length of an orthographic projection of said inner edges (22, 32) on a projection plane perpendicular to the axis.

4. The anastomotic device (10) according to claim 1, wherein the contact surfaces (21, 31) comprise knurlings (33) to increase friction.

5. The anastomotic device (10) according to claim 1, wherein said coupling means (40) are suitable to generate and maintain a clamping force in the axial direction between the first ring (20) and the second ring (30).

6. The anastomotic device (10) according to claim 5, wherein the coupling means (40) are of a snap type.

7. The anastomotic device (10) according to claim 6, wherein the coupling means (40) comprise at least one pin (43) that from the contact surface (31) of the second ring (30) projects in the axial direction.

8. The anastomotic device (10) according to claim 7, wherein the coupling means (40) comprise at least one seat (42) that is formed on the first ring (20), having an axial development and being suitable to accommodate said at least one pin (43).

9. The anastomotic device (10) according to claim 8, wherein the pin (43) comprises teeth (44) that are distributed along an operating coupling tract (46).

10. The anastomotic device (10) according to claim 9, wherein the seat (42) comprises elastic tabs (45) that are suitable to engage the teeth (44) and slide along the operating coupling tract (46) only in one direction.

11. The anastomotic device (10) according to claim 8, wherein the pins (43) and the respective seats (42) are in a number of two.

12. The anastomotic device (10) according to claim 8, further comprising holes (52, 53) suitable for guide wires to pass therethrough, which are required for carrying out the operation of endoluminal or laparoscopic implantation.

13. The anastomotic device (10) according to claim 12, wherein the holes (52, 53) are formed on both rings (20, 30) such that the rings (20, 30) are allowed to be properly approached to each other simply by sliding along the guide wires.

14. The anastomotic device (10) according to claim 13, wherein the seats (42) act as holes (52) for the guide wires to be passed therethrough.

15. The anastomotic device (10) according to claim 12, wherein the holes (53) for the passage of the guide wires run through the inside of the pins (43).

16. The anastomotic device (10) according to claim 5, wherein the coupling means (40) are at least partially made of bio-absorbable or biofragmentable material.

17. The anastomotic device (10) according to claim 1, wherein the contact surfaces (21, 31) of the two rings (20 and 30) are mutually inclined.

18. The anastomotic device (10) according to claim 17, wherein the mutual inclination of the contact surfaces (21, 31) is such that a spacing is provided between the contact surfaces (21, 31), which is variable in the radial direction.

19. The anastomotic device (10) according to claim 1, wherein on one of the rings (20, 30) there is arranged a knife (50).

20. The anastomotic device (10) according to claim 19, wherein the knife (50) is arranged at the inner edge (22, 32) of the contact surface (21, 31).

21. The anastomotic device (10) according to claim 19, wherein the knife (50) has an extension in the axial direction such that it can cooperate, when the rings (20, 30) are being approached, with the inner edge (32, 22) of the contact surface (31, 21) of the other ring (30, 20).

22. The anastomotic device (10) according to claim 21, wherein the knife (50) that is placed on one of the rings (20, 30) and the inner edge (32, 22) of the contact surface (31, 21) of the other ring (30, 20) acts as an annular shear.

23. The anastomotic device (10) according to claim 1, which is at least partially made of a bio-absorbable or biofragmentable material.

* * * * *